United States Patent
Nakanishi

[11] Patent Number: 5,816,803
[45] Date of Patent: Oct. 6, 1998

[54] WATER INJECTION TYPE DENTAL HANDPIECE

[75] Inventor: Takasuke Nakanishi, Kanuma, Japan

[73] Assignee: Nakanishi, Inc., Tochigi, Japan

[21] Appl. No.: 657,811

[22] Filed: May 31, 1996

[30] Foreign Application Priority Data

May 31, 1995 [JP] Japan ..................... 7-133142

[51] Int. Cl.⁶ .................................................. A61C 1/02
[52] U.S. Cl. ............................................. 433/82; 433/115
[58] Field of Search ................... 433/82–85, 87, 433/115

[56] References Cited

U.S. PATENT DOCUMENTS

| | | | |
|---|---|---|---|
| 2,400,912 | 5/1946 | Britt et al. | 433/125 |
| 5,022,857 | 6/1991 | Matsutani et al. | 433/85 |
| 5,275,558 | 1/1994 | Seney | 433/82 |
| 5,433,604 | 7/1995 | Lawdgraf | 433/82 |
| 5,531,596 | 7/1996 | Melde | 433/82 |

FOREIGN PATENT DOCUMENTS

| | | | |
|---|---|---|---|
| 610113 | 8/1994 | European Pat. Off. | 433/82 |
| 1297809 | 6/1969 | Germany | 433/82 |

*Primary Examiner*—Ralph Lewis
*Attorney, Agent, or Firm*—Malcolm B. Wittenberg

[57] ABSTRACT

A center injection type dental handpiece contains a cutting bar having a hollow axially penetrating the bar, holding means for detachably holding the bar, rotating means for rotating the bar, a water injection nozzle communicating with a cooling water feed source. The water injection nozzle is inserted into the hollow of the bar for injecting a cooling water from tip of the bar. The handpiece further contains a packing for sealing a gap between the outer periphery of the nozzle and the inner periphery of the bar at the proximal end of the bar.

4 Claims, 3 Drawing Sheets

WATER INJECTION TYPE DENTAL HANDPIECE

BACKGROUND OF THE INVENTION

The present invention relates to a water injection type dental handpiece, and more particularly to a water injection type dental handpiece capable of injecting water through a central bore in a cutting burr which can be used for dental implant or the like.

A water injection type handpiece has hitherto been used for drilling and tapping a tooth in dental implantation. In such a prior art handpiece, as shown in FIG. 3, a cutting burr 1 such as a drill having a bore 2 axially extending in the center thereof is detachably secured in a head 10 and rotated. A water injection nozzle 20 communicating with a cooling water feed source (not shown) is inserted into the bore 2 from the proximal end 1' of the burr 1, so that the cooling water can be injected into a cutting site through an injection port 2' at the distal end 1" of the burr 1.

In such a conventional water injection type handpiece, however, when the injection port 2' of the burr 1 abuts the cutting site and blocked, the cooling water flows in a reverse direction through a small gap between the outer surface 10' of the injection nozzle 20 and the inner surface of the bore 2, and leaks out of the burr 1 into the interior of the head 10. Such water leakage may have an adverse effect on bearings 16, or may generate rust on internal parts such as a gear 15. As a result, cutting efficiency and durability of the handpiece may be lowered.

SUMMARY OF THE INVENTION

It is therefore an object of the present invention to provide a water injection type dental handpiece wherein leakage of cooling water from the proximal end of the burr into the interior of the head is prevented.

The present invention provides an improvement over conventional water injection type handpiece 5 wherein a water injection nozzle communicating with a cooling water feed source is inserted into a bore in a burr for injecting water through the distal end of the burr.

Toward the fulfillment of the above and other objects, according to the present invention, there is provided a water injection type dental handpiece, which comprises a cutting burr having proximal and distal ends and an outer surface and further having a bore axially extending through the burr. The bore is provided with an inner surface and proximal and distal opening at the proximal and distal ends of the burr. Means are provided for detachably holding the burr and for rotating the burr. The means for detachably holding the burr includes a push-button having an opening with an edge.

The present invention further includes a water injection nozzle having two ends and an outer surface. The nozzle communicates with a cooling water feed source at one end and extends into and communicates at the other end with the above-noted bore in the burr through the proximal opening of the bore for transmitting cooling water from the feed source to the bore in the burr. The invention further includes packing for sealing a gap between the outer surface of the nozzle and the inner surface of the burr at the proximal end of the burr, the packing surface having a groove mating with the edge of the opening in the push-button for sealingly fitting within the opening in the push-button.

DETAILED DESCRIPTION OF THE INVENTION

Figure 1:
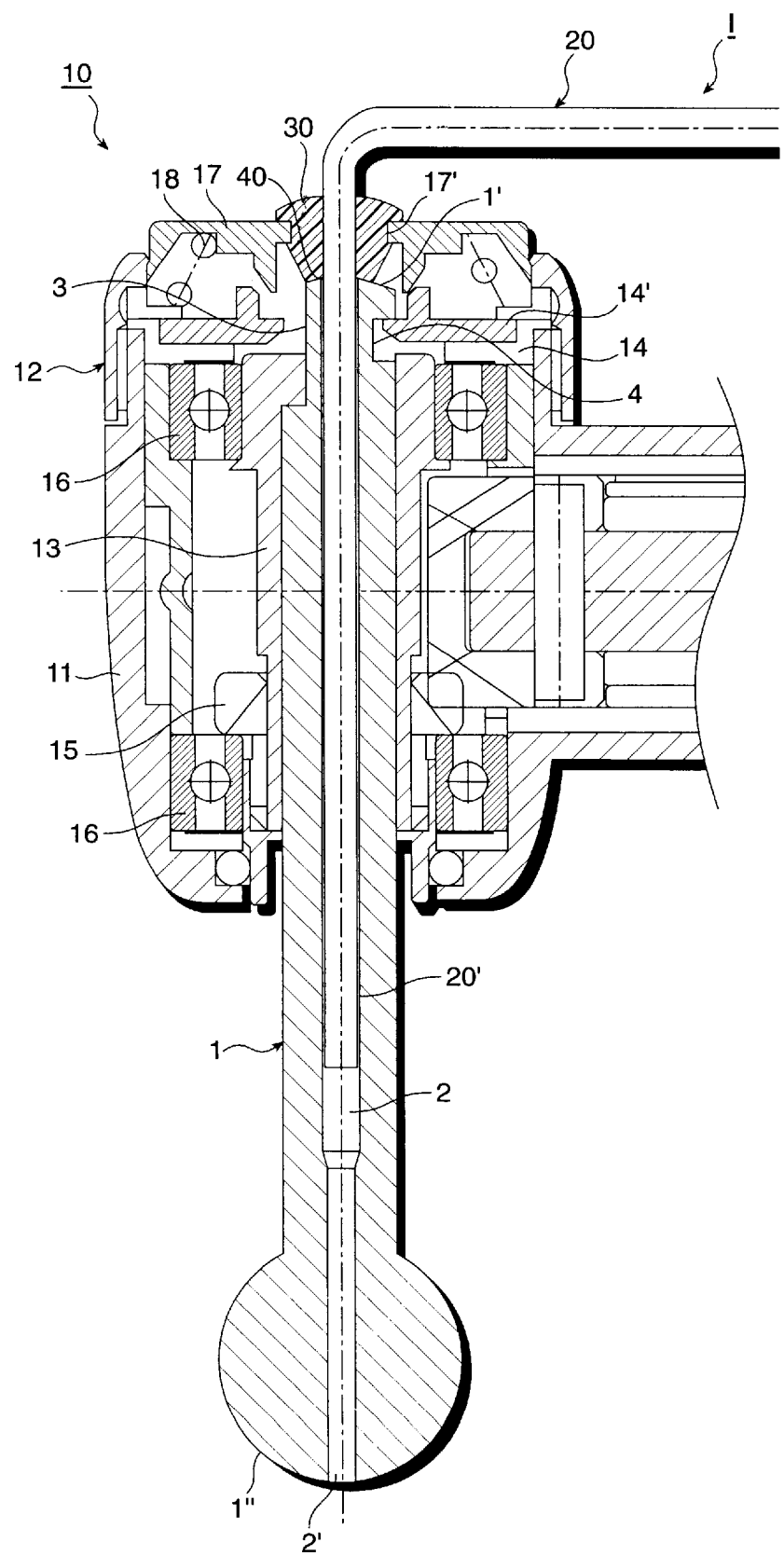
FIG. 1 is a sectional view of a head of a water injection type dental handpiece of the present invention.
Figure 3:
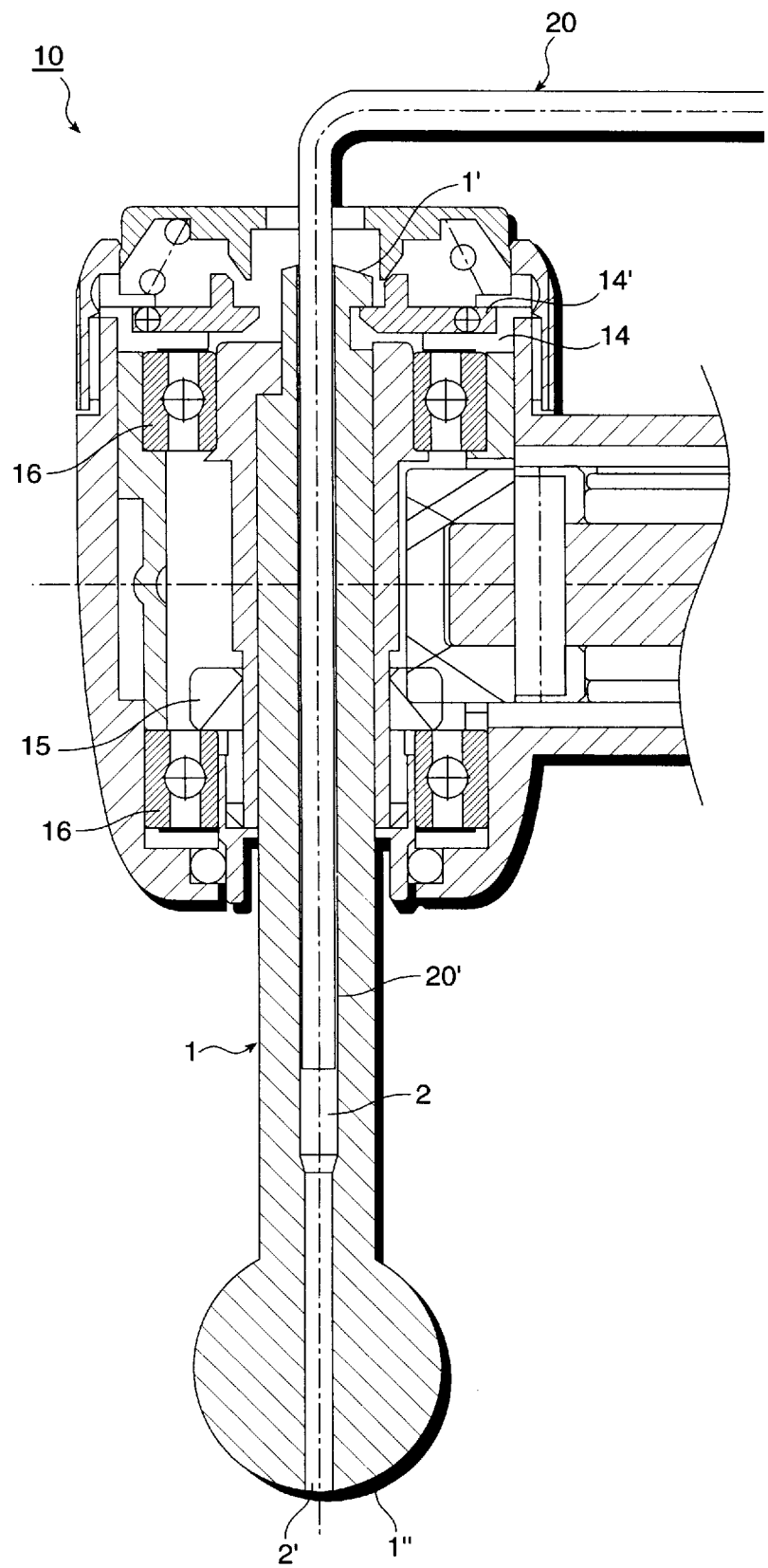
FIG. 3 is a sectional view of a conventional water injection type dental handpiece.

FIG. 1 is a sectional view of a head 10 of a water injection type dental handpiece I of the invention. Same parts as in FIG. 3 are identified with the same reference numerals.

The handpiece I is a contra angle handpiece of a push type, wherein cutting burr 1 (schematically shown) of a latch type is detachably held and rotated in head 10. The cutting burr 1 has bore 2 extending in the axial direction of the burr 1 in the center thereof, into which water injection nozzle 20 to be described later is inserted for transmitting cooling water to the distal end of the burr. Notch 3 and detent groove 4 are provided near the proximal end of burr 1.

The head 10 has housing 11, which contains burr tube 13, chuck device 14, gear 15, and upper and lower ball bearings 16. The burr tube 13 receives burr 1 therein for unrotatably holding the burr in cooperation with notch 3 on burr 1. The chuck device 14 includes latch plate 14' biased radially inwardly by a spring (not shown) into engagement with detent groove 4 on burr 1 for securing burr 1 in place. The gear 15 is fixed on the outer surface of burr tube 13 in the lower (distal) portion thereof and driven by a motor (not shown) to rotate the burr tube with burr 1. The upper and lower ball bearings 16 rotatably support burr tube 13 and gear 15.

The head cap 12 is screwed onto head housing 11, and provided with push-button 17 which is biased upwardly by spring 18. By pushing button 17 downwardly, latch plate 14' of chuck device 14 is moved radially outwardly and opened, and burr 1 is released from chuck device 14.

The push-button 17 has opening 17' through which water injection nozzle 20 is extended as will be described later. Also placed in opening 17' is packing 30 for sealing a gap between the edge of opening 17' and the outer surface of nozzle 20 as will be described below.

Figure 2:
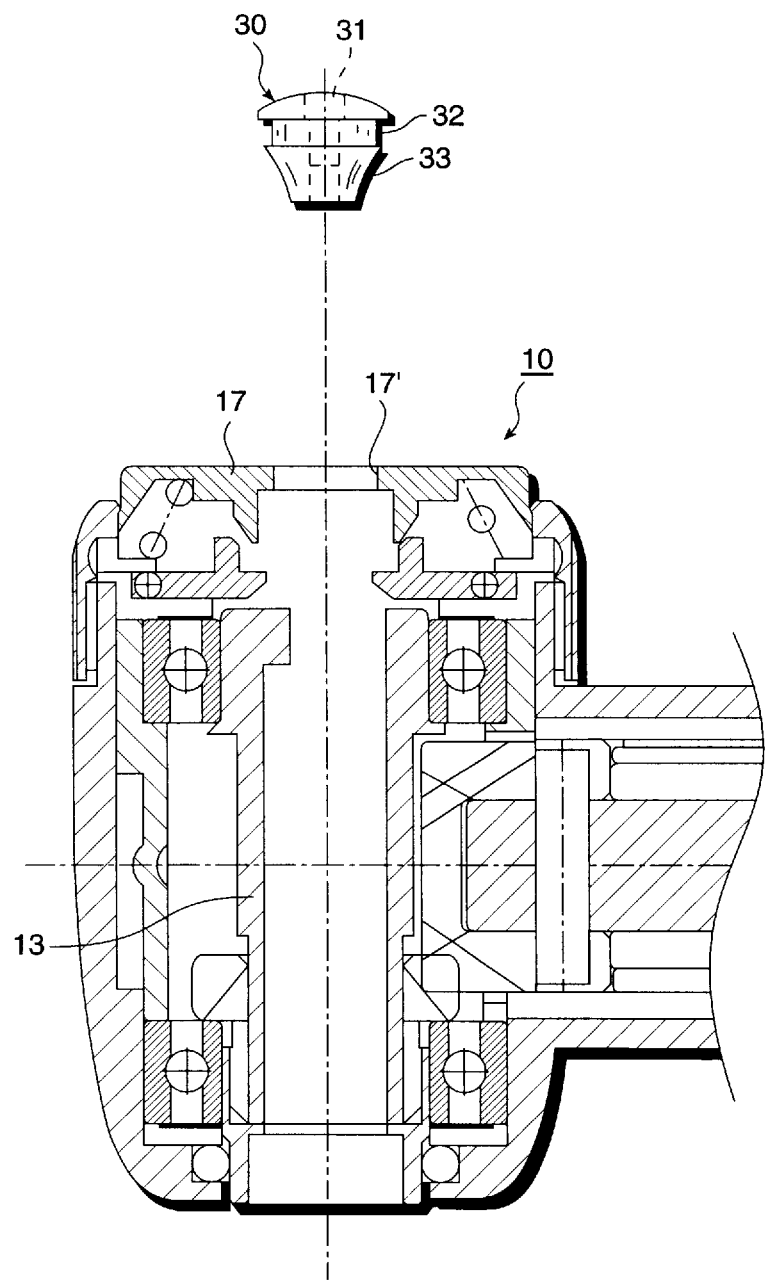
FIG. 2 is a sectional view, partially exploded, of the head and a packing of the handpiece of the present invention, wherein a burr and an injection nozzle are removed for the sake of clarity.

As shown in FIG. 2, packing 30 has a bore 31 through which injection nozzle 20 is extended. On the outer surface of packing 30, annular groove 32 is provided which mates with the edge of opening 17' in push-button 17 for sealing the gap between the edge of opening 17' and outer surface 20' of nozzle 20. The lower portion 33 of packing 30 below groove 32 has a downwardly tapered surface for sealing the gap between outer surface 20' of nozzle 20 and the inner surface of bore 2 in the burr 1 at the proximal end of burr 1.

The packing 30 is made of an elastic material, so that it can easily be attached to and detached from opening 17' in push-button 17. Preferred examples of the elastic material may include nitrile rubber, silicone rubber, and fluororubber.

Water injection nozzle 20 communicates with a cooling water source (not shown) for transmitting cooling water from the source to the interior of the bore in the burr. Nozzle 20 is extended through bore 31 in the packing 30 fit in opening 17' in push-button 17, and then further extended into bore 2 in burr 1 for transmitting cooling water to distal end 1" of the burr 1 for injection through the injection port 2'.

According to the present invention, lower portion 33 of packing 30 seals the gap between outer surface 20' of injection nozzle 20 and inner surface of bore 2 in burr 1 at the proximal end 1' of burr 1 with a slight pressure. Therefore, even if injection port 2' at distal end 1" of burr 1 is blocked, the resulting pressure is not released from proximal end 1' of burr 1. Accordingly, gap 40 between outer surface 20' of the injection nozzle 20 and inner surface of bore 2 in burr 1 will not serve as a leakage path for the cooling water, and thus the leakage of the cooling water into the interior of the head 10 is prevented.

Further, since the handpiece I of the water injection type is intended for use in tapping operation, the rotational speed of burr 1 is low, so that the packing 30 in contact with the burr 1 is hardly worn due to friction between proximal end 1' of the burr and packing 30.

Although the present invention has been described with reference to the preferred embodiment, it should be understood that various modifications and variations can be easily made by those skilled in the art without departing from the spirit of the invention. Accordingly, the foregoing disclosure should be interpreted as illustrative only and is not to be interpreted in a limiting sense. The present invention is limited only by the scope of the following claims.

What is claimed is:

1. A water injection type dental handpiece comprising:

a cutting burr having proximal and distal ends and an outer surface, said cutting burr having a bore axially extending through said burr, said bore having an inner surface and proximal and distal openings at the proximal and distal ends of the burr, respectively, means for detachably holding said burr, said means including a push-button having an opening with an edge, means for rotating said burr, a water injection nozzle having two ends and an outer surface, said nozzle communicating with a cooling water feed source at one end, said nozzle extending into and communicating at the other end with said bore in the burr through said proximal opening of said bore for transmitting cooling water from the feed source to the bore in the burr, and packing for sealing a gap between the outer surface of the nozzle and the inner surface of the burr at the proximal end of the burr, said packing having a groove mating with the edge of said opening in the push-button for sealingly fitting in the opening in the push-button.

2. The water injection type dental handpiece of claim 1, wherein said packing has a bore through which said water injection nozzle extends.

3. The water injection type dental handpiece of claim 1, wherein said means for detachably holding said burr further comprises a chuck device for engagingly holding the burr, said push-button engaging said chuck device when said push-button is pressed down to disengage the burr from the chuck device to permit releasing of the burr, said water injection nozzle extending through said opening of the push-button.

4. The water injection type dental handpiece of claim 3 wherein said burr has a detent groove on its outer surface near its proximal end, and wherein said chuck device comprises a latch plate, said latch plate detachably engaging the detent groove for holding the burr.

* * * * *